United States Patent [19]
Yonkers

[11] 3,985,383
[45] Oct. 12, 1976

[54] INDEXING DEVICE
[76] Inventor: John L. Yonkers, 2030 Sunset Ridge Road, Northbrook, Ill. 60062
[22] Filed: Mar. 3, 1975
[21] Appl. No.: 554,676

[52] U.S. Cl. .................................. 294/25; 2/21
[51] Int. Cl.² .................... A41D 13/08; A61F 13/10
[58] Field of Search ............ 294/1 R, 25; 2/21, 163; 15/227; 128/153, 157; 206/447, 460; 223/101; 273/81 B, 81 D, 166

[56] References Cited
UNITED STATES PATENTS

| | | | |
|---|---|---|---|
| 942,003 | 11/1909 | Marsh | 294/25 |
| 1,844,507 | 2/1932 | Gifford | 294/25 |
| 1,863,960 | 6/1932 | Aronson | 2/21 |
| 3,191,824 | 6/1965 | Burr | 2/21 X |
| 3,283,888 | 11/1966 | Scott | 294/25 X |

Primary Examiner—Johnny D. Cherry
Attorney, Agent, or Firm—Mason, Kolehmainen

[57] ABSTRACT

An indexing device includes a layer of film and pressure sensitive adhesive material located on at least a portion of one side of the layer of film to enable the layer of film to adhere to an object such as a finger. The indexing device further includes material having a very high coefficient of friction with respect to the objects to be indexed disposed upon at least a portion of the second side of the film layer. By sliding the material disposed on the second side of the indexing device across a planar object such as a sheet of paper, a substantial frictional force is developed that resists the relative movement of the indexing device and the planar object. This resistance to relative movement serves to index or separate the planar object from adjacent planar objects.

4 Claims, 6 Drawing Figures

U.S. Patent   Oct 12, 1976   3,985,383
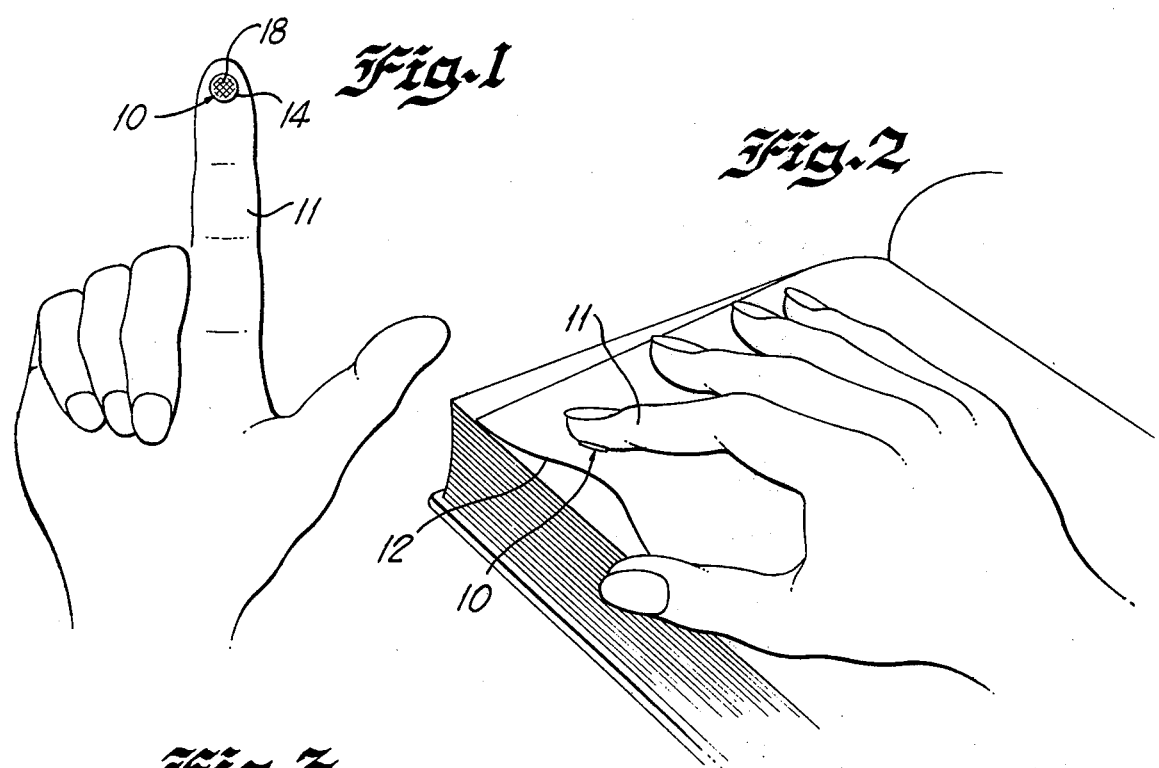
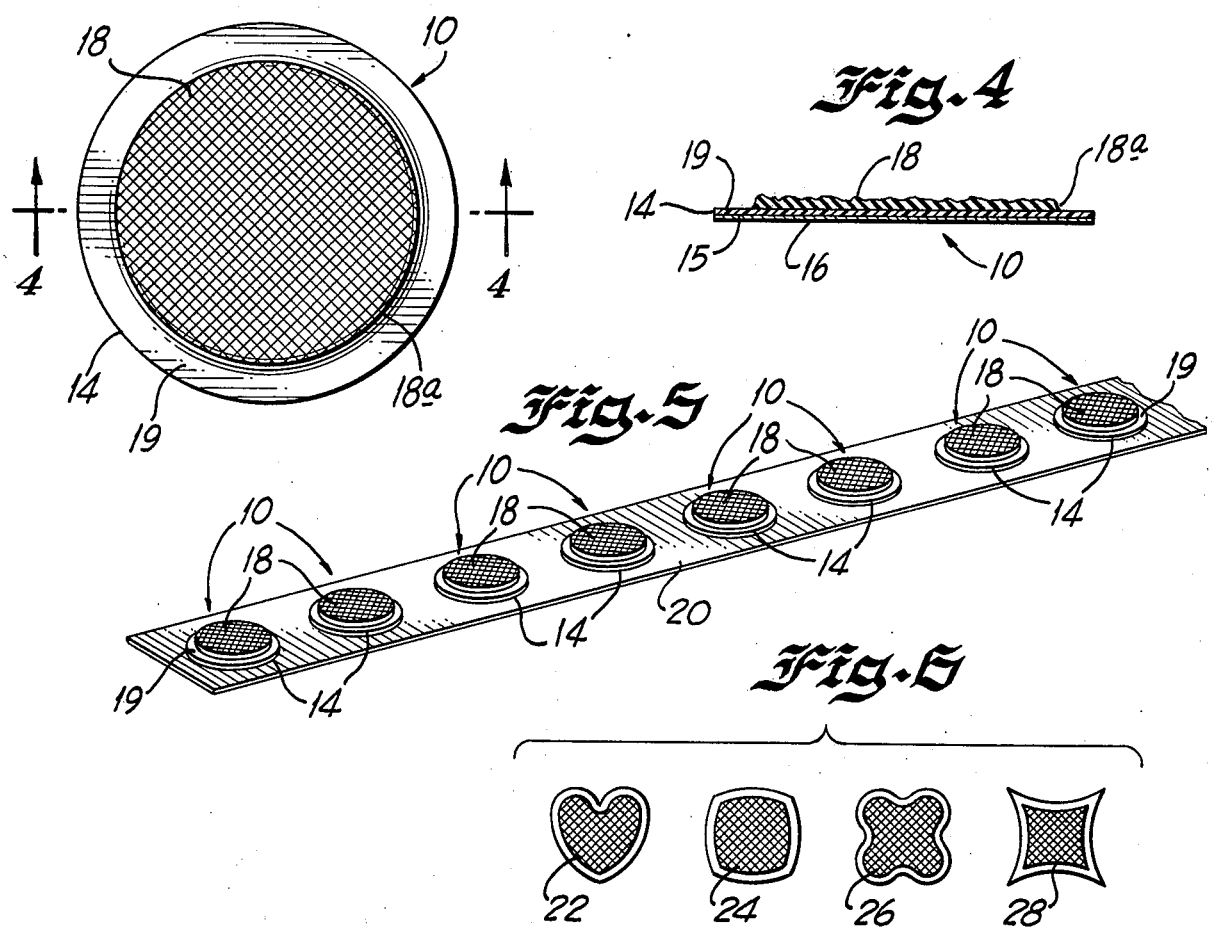
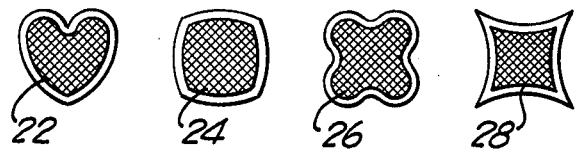

3,985,383

INDEXING DEVICE

BACKGROUND OF THE INVENTION

1. Field of the Invention

The apparatus of the present invention generally relates to a new and improved apparatus for indexing or separating adjacent planar objects and to a new and improved method for indexing or separating such planar objects and, more particularly, to a new and improved device and method for separating or indexing adjacent sheets of paper.

2. Description of the Prior Art

In the handling of papers in clerical and stenographic work, rubber shells, shaped like the end of a finger, are used to separate or index sheets of paper. These devices, though widely used throughout the business world, are characteristically unattractive in appearance, produce skin irritation in hot weather and become soiled with use. Such rubber shells are also extremely cumbersome to use because they must be removed by the user when a different task such as typing is commenced. Upon completion of this different task, a rubber shell must be replaced on the finger to allow the user to return to separating or indexing items, such as sheets of paper. As a result, the user is inconvenienced by the process of putting on and removing the rubber shell as the user changes from task to task.

Typically, prior art rubber shells are of the type formed from rubber or similar material having cross hatching around its entire periphery to increase its traction. This type of shell is formed in the shape of the end of a finger so that it may be worn over the tip of a user's finger. Since these prior art shells are placed over the tip of the finger, the entire shell is made of traction or rubber material even though all portions of the shell are not used against a workpiece at the same time. This configuration necessitates the use of a greater amount of traction material than is actually necessary, thereby increasing the cost of production. Moreover, the shape of the shell further increases the complexity of manufacturing and thus the cost of production.

Since the rubber shell covers the entire tip of the finger, little or no air is vented to the portion of the finger beneath the shell. This results in increased perspiration which attacks the traction material of the shell resulting in rapid deterioration. Additionally, the universal size of the rubber shell, which is necessitated by mass production, results in a loose fit on small fingers making them difficult to use, or a tight fit on large fingers causing discomfort and limiting the period of wear.

SUMMARY OF THE INVENTION

An object of the present invention is to provide a new and improved device for indexing or separating adjacent planar objects.

Another object of the present invention is to provide a new and improved method for indexing or separating adjacent planar objects.

A further object of the present invention is to provide a new and improved device for indexing or separating adjacent planar objects in which the device need not be removed to perform other tasks.

An additional object of the present invention is to provide a new and improved device for indexing or separating adjacent planar objects that is attractive in appearance and does not readily produce skin irritation.

Briefly, the present invention is directed to a new and improved device for indexing or separating adjacent planar objects, such as sheets of paper. This device is referred to as an indexing device and includes a layer of film which can be of several different configurations, but is of a size such that it may be easily placed on a finger tip. A pressure sensitive adhesive material that enables the layer of film to be securely mounted onto the tip of a finger or other object is disposed on one side of the layer of material. Since the indexing device is small and adheres to a fingertip, the user can alternate tasks without removing the device.

Preferably, a mass of traction material is disposed on the other side of the layer of film in substantially the same configuration as the layer of film, but of a lesser cross-sectional area. Advantageously, the indexing device is removably mounted onto a continuous strip of backing material and is simply removed from the backing material and placed on a finger or similar object for use in indexing objects.

BRIEF DESCRIPTION OF THE DRAWING

The above and other objects and advantages and novel features of the present invention will become apparent from the following detailed description of a preferred embodiment of the invention illustrated in the accompanying drawing wherein:

FIG. 1 is an elevational view of a preferred embodiment of the indexing device constructed and used in accordance with the principles of the present invention;

FIG. 2 is an illustrative view of the manner in which the device of FIG. 1 may be used;

FIG. 3 is an enlarged top plan view of the device of FIG. 1;

FIG. 4 is an enlarged, cross-sectional view of the device of FIG. 1 taken along line 4—4 of FIG. 3;

FIG. 5 is an elevational view of a plurality of the devices of FIG. 1 mounted on a continuous backing strip; and FIG. 6 is an enlarged elevational view of a plurality of alternate embodiments of the device of FIG. 1.

DESCRIPTION OF THE PREFERRED EMBODIMENT

With reference to FIGS. 1–4 of the drawing, there is illustrated a new and improved indexing device 10 constructed in accordance with the principles of the present invention. The indexing device 10 may be attached to the finger 11 of an individual wishing to index or separate adjacent planar objects 12, such as sheets of paper, as illustrated in FIG. 2.

The indexing device 10 includes a layer of plastic film 14 which may be formed in any desired configuration, for example, in a preferred embodiment, it may have a circular outer periphery in the shape of a disc as illustrated in FIG. 3. The layer of plastic film 14 serves as the support element of the indexing device 10 and may be flexible so as to conform easily to the contour of the finger 11. Alternately, the layer of plastic film 14 may be rigid to serve not only as a support element but also as protection against punctures caused by the objects being indexed or separated.

In accordance with an important feature of the present invention, a first side or surface 15 of the layer of plastic film 14 is coated with a pressure sensitive adhesive material 16 (FIG. 4) to enable the layer of plastic film 14 to be attached to the finger 11 or to another object. Through the use of the adhesive material 16, no other supporting or attaching means is required during the use of the indexing device 10. The adhesive material 16 can be of any type well known in the art and may be of the same material as that used on ordinary adhesive tape. In addition, the adhesive material 16 may cover either a portion of the side 15 of the film 14 or the entire side 15 of the film 14 depending on the adhesive qualities of the material 16 and the desirability of securing the complete side 15 of the film 14 onto the finger 11.

In accordance with a further important feature of the present invention, a mass of traction material 18 having a very high coefficient of friction with respect to the objects to be indexed is disposed on a second side or surface 19 of the film 14. The mass of traction material 18 may be of the same general configuration as the layer of plastic film 14 and may be attached thereto by cement. The mass of traction material 18 may, in a specific embodiment, be an elastomeric material such as foam and sponge rubber containing glycerine; or, in an alternate embodiment, the mass of traction material 18 may be smooth rubber stock that has been cross-cut or hatched (FIG. 3) to increase its traction capability. The mass of traction material 18 may alternately comprise rubber threads which are released from a liquid rubber container onto the plastic layer of film 14.

It is believed that the excellent adhesion of the layer of plastic film 14 to the finger 11 results from the extension of the outer periphery of the layer of plastic film 14 beyond the outer periphery of the mass of traction material 18, that is, the mass of traction material 18 has a smaller cross-sectional area than the cross-sectional area of the layer of plastic film 14.

Further, it has been determined by experimentation that if the mass of traction material 18 is relatively thick, better adhesion to the finger 11 by the device 10 results if a peripheral edge 18a (FIG. 4) of the mass of traction material 18 is tapered.

A specific example of a preferred embodiment of the present invention is a layer of plastic film 14 formed in the shape of a disc and having a diameter of 5/16 inch. A mass of traction material 18 formed in the shape of a disc from foam and sponge rubber containing glycerine and having a diameter of ¼ inch is secured to the side 19 of the layer of plastic film 14. In addition, pressure sensitive adhesive material 16 is disposed on the entire side 15 of the layer of plastic film 14.

Another embodiment of the indexing device 10 includes a layer of plastic film 14 which has a first side or surface 15 upon which adhesive material 16 is applied. The peripheral edge of the layer of plastic film 14 is tapered from its other or second side or surface 19 to its first side 15 such that the layer of plastic film 14 serves both as a support element for the adhesive material 16 and as a mass of traction material for indexing objects. The layer of plastic film 14 in this embodiment of the present invention has a frustoconical shape in which the side or surface 19 serves as the traction surface. The side or surface 19 may be cross-cut or hatched in a manner similar that shown in FIG. 3 to increase its traction capability.

A plurality of indexing devices 10 can be attached to a continuous backing strip 20 (FIG. 5) through the use of the adhesive material 16 and placed in dispensing containers such as those commonly used by adhesive tag manufacturers. When an indexing device 10 is to be used, it may be separated from the continuous backing strip 20 and placed on the finger 11.

Further, alternate embodiments of the indexing device 10 include variations of color and shape (FIG. 6) of both the mass of traction material 18 and the layer of plastic film 14. For example, the device 10 may be formed in the shape of a heart 22, a square 24, a clover 26 or a diamond 28. Each of these alternate embodiments of the device 10 is constructed in essentially the same manner as that set forth above with respect to the preferred embodiment and may be attached to a continuous backing strip 20.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. An indexing device comprising
   a layer of film,
   pressure sensitive adhesive material attached to a first side of said film, and
   traction material attached to a second side of said film, said layer of film being more rigid than said traction material, said traction material being of a configuration slightly smaller than that of said layer of film such that an edge of said layer extends beyond the outer periphery of said traction material.

2. An indexing device as defined in claim 1 wherein said configuration of said film and said traction material comprises a substantially circular outer periphery.

3. An indexing device as defined in claim 2 wherein said traction material comprises sponge rubber containing glycerine.

4. An indexing device comprising a layer of film, traction material attached to a first side of said film, said layer of film being more rigid than said traction material, said traction material comprising a mass of elastomeric material having an upper and a lower surface and first and second pluralities of cuts disposed on said upper surface, said first plurality of cuts being disposed transverse to said second plurality of cuts, the outer periphery of said mass of said elastomeric material being tapered from said lower surface to said upper surface, the area of said lower surface being substantially greater than the area of said upper surface, said layer of film being attached to said lower surface and having a slightly larger area than the area of said lower surface such that a portion of said layer extends beyond the periphery of said mass, and pressure sensitive adhesive material attached to a second side of said film.

* * * * *